(12) United States Patent
Moloney et al.

(10) Patent No.: US 12,302,949 B2
(45) Date of Patent: May 20, 2025

(54) DELIVERY PREDICTION APPARATUS AND METHOD

(71) Applicant: NICOVENTURES TRADING LIMITED, London (GB)

(72) Inventors: Patrick Moloney, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 384 days.

(21) Appl. No.: 17/754,940

(22) PCT Filed: Sep. 17, 2020

(86) PCT No.: PCT/GB2020/052245
§ 371 (c)(1),
(2) Date: Apr. 15, 2022

(87) PCT Pub. No.: WO2021/074577
PCT Pub. Date: Apr. 22, 2021

(65) Prior Publication Data
US 2022/0361586 A1 Nov. 17, 2022

(30) Foreign Application Priority Data
Oct. 16, 2019 (GB) ........................ 1914944

(51) Int. Cl.
*A24F 40/53* (2020.01)
*A24F 40/10* (2020.01)
(Continued)

(52) U.S. Cl.
CPC .............. *A24F 40/53* (2020.01); *A24F 40/10* (2020.01); *A24F 40/65* (2020.01); *A61B 5/14546* (2013.01)

(58) Field of Classification Search
CPC .......... A24F 40/53; A24F 40/10; A24F 40/65; A24F 40/50; A61B 5/14546; G06Q 10/04; G06Q 50/10
See application file for complete search history.

(56) References Cited

U.S. PATENT DOCUMENTS 10,834,972 B2 * 11/2020 Mironov .................. H05B 6/38
11,452,826 B2 * 9/2022 Leadley .................. A24F 40/40
(Continued)

FOREIGN PATENT DOCUMENTS

EP 3536177 A1 9/2019
JP 2019521739 A 8/2019
(Continued)

OTHER PUBLICATIONS

International Search Report and Written Opinion for Application No. PCT/GB2020/052245, mailed on Nov. 25, 2020, 13 pages.
(Continued)

*Primary Examiner* — Truc T Nguyen
(74) *Attorney, Agent, or Firm* — BURR & FORMAN LLP (57) ABSTRACT

An aerosol provision system generates aerosol from an aerosol generating material for user inhalation. The system includes a computer configured to estimate user demand for an active ingredient within the generated aerosol, based on one or more inhalation actions of the user during an immediately preceding inhalation session, where an inhalation session being no more than one hour long. The computer adjusts one or more operational parameters of the aerosol provision system responsive to the estimated user demand, and adapts aerosol provision for the next inhalation action.

24 Claims, 4 Drawing Sheets

(51) Int. Cl.
*A24F 40/65* (2020.01)
*A61B 5/145* (2006.01)

(56) References Cited

U.S. PATENT DOCUMENTS

| | | |
|---|---|---|
| 2017/0079329 A1 | 3/2017 | Zitzke |
| 2019/0167927 A1 | 6/2019 | Dagnello et al. |
| 2019/0191773 A1* | 6/2019 | Alelov ................ A61M 15/008 |
| 2019/0247598 A1* | 8/2019 | Yamada .................. A24F 47/00 |
| 2020/0085105 A1* | 3/2020 | Barbaric ............. G06F 16/9035 |
| 2021/0000184 A1* | 1/2021 | Moloney ................ A24F 40/57 |
| 2024/0393878 A1* | 11/2024 | Kim ........................ G06F 3/015 |

FOREIGN PATENT DOCUMENTS

| | | |
|---|---|---|
| WO | WO-9215353 A2 | 9/1992 |
| WO | WO-2007008825 A2 | 1/2007 |
| WO | WO-2013098398 A2 | 7/2013 |
| WO | 2015131991 A1 | 9/2015 |
| WO | WO-2015189556 A1 | 12/2015 |
| WO | WO-2016091658 A1 | 6/2016 |
| WO | WO-2019104227 A1 | 5/2019 |
| WO | 2019173923 A1 | 9/2019 |

OTHER PUBLICATIONS

English Translation of Office Action mailed on Oct. 30, 2024 for Korean Application No. 10-2022-7012737, all enclosed pages cited.

* cited by examiner

Figure 5 s710 — Estimate a user demand for an active ingredient within the generated aerosol, based on one or more inhalation actions of the user during an immediately preceding inhalation session, an inhalation session being no more than one hour long s720 — Adjust one or more operational parameters of the aerosol provision system responsive to the estimated user demand, to adapt aerosol provision for the next inhalation action

Figure 6

DELIVERY PREDICTION APPARATUS AND METHOD

PRIORITY CLAIM

The present application is a National Phase entry of PCT Application No. PCT/GB2020/052245, filed Sep. 17, 2020, which claims priority from Patent Application No. 1914944.2, filed Oct. 16, 2019, which is hereby fully incorporated herein by reference.

FIELD

The present disclosure relates to a delivery prediction apparatus and method, in particular for electronic aerosol provision systems such as electronic cigarettes.

BACKGROUND

Electronic aerosol provision systems such as electronic cigarettes (e-cigarettes) generally contain a reservoir of a source liquid containing a formulation, typically including nicotine, from which an aerosol is generated, e.g., through heat vaporization. An aerosol source for an aerosol provision system may thus comprise a heater having a heating element arranged to receive source liquid from the reservoir, for example through wicking/capillary action. Other source materials may be similarly heated to create an aerosol, such as botanical matter, or a gel comprising an active ingredient and/or flavoring. Hence more generally, the e-cigarette may be thought of as comprising or receiving a payload for heat vaporization.

While a user inhales on the device, electrical power is supplied to the heating element to vaporize the aerosol source (a portion of the payload) in the vicinity of the heating element, to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol source. There is a flow path connecting between the aerosol source and an opening in the mouthpiece so that air drawn past the aerosol source continues along the flow path to the mouthpiece opening, carrying some of the aerosol from the aerosol source with it. The aerosol-carrying air exits the aerosol provision system through the mouthpiece opening for inhalation by the user.

Usually an electric current is supplied to the heater when a user is drawing/puffing on the device. Typically, the electric current is supplied to the heater, e.g. resistance heating element, in response to either the activation of an airflow sensor along the flow path as the user inhales/draw/puffs or in response to the activation of a button by the user. The heat generated by the heating element is used to vaporize a formulation. The released vapor mixes with air drawn through the device by the puffing consumer and forms an aerosol. Alternatively or in addition, the heating element is used to heat but typically not burn a botanical such as tobacco, to release active ingredients thereof as a vapor/aerosol.

The amount of vaporized/aerosolized payload inhaled by the user will depend at least in part on how long and how deeply the user inhales and, over a period of time, how frequently the user inhales as well. In turn, these user behaviors may be influenced by their mood.

In particular, it would be useful to estimate the user's current demand for inhaled payload.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

SUMMARY

In a first aspect, an aerosol provision system is provided to generate aerosol from an aerosol generating material for user inhalation, the system comprising a computer configured to estimate a user demand for an active ingredient within the generated aerosol, based on one or more inhalation actions of the user during an immediately preceding inhalation session, an inhalation session being no more than one hour long; and adjust one or more operational parameters of the aerosol provision system responsive to the estimated user demand, to adapt aerosol provision for the next inhalation action.

In another aspect, an aerosol provision method is provided in which an adjustment of one or more operational parameters of the aerosol provision system responsive to the estimated user demand is responsive to an estimate of the current blood concentration of the active ingredient in the user. In another aspect, an adjustment of one or more operational parameters of the aerosol provision system responsive to the estimated user demand is responsive to a limit on the current blood concentration of the active ingredient in the user.

It is to be understood that both the foregoing general summary of the disclosure and the following detailed description are exemplary, but are not restrictive, of the disclosure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings.

DETAILED DESCRIPTION OF THE EMBODIMENTS

An electronic aerosol provision system and method are disclosed herein. In the following description, a number of specific details are presented in order to provide a thorough understanding of the embodiments of the present disclosure. It will be apparent, however, to a person skilled in the art that these specific details need not be employed to practice embodiments of the present disclosure. Conversely, specific details known to the person skilled in the art are omitted for the purposes of clarity where appropriate.

As described above, the present disclosure relates to an aerosol provision system (e.g., a non-combustible aerosol provision system) or electronic vapor provision system (EVPS), such as an e-cigarette. Throughout the following description the term "e-cigarette" is sometimes used but this term may be used interchangeably with (electronic) aerosol or vapor provision system. Similarly the terms 'vapor' and 'aerosol' are referred to equivalently herein.

Generally, the electronic vapor or aerosol provision system may be an electronic cigarette, also known as a vaping device or electronic nicotine delivery system (END), although it is noted that the presence of nicotine in the aerosolizable material is not a requirement. In some embodiments, a non-combustible aerosol provision system is a tobacco heating system, also known as a heat-not-burn system. In some embodiments, the non-combustible aerosol provision system is a hybrid system to generate aerosol using a combination of aerosolizable materials, one or a plurality of which may be heated. Each of the aerosolizable materials may be, for example, in the form of a solid, liquid, or gel, and may or may not contain nicotine. In some embodiments, the hybrid system comprises a liquid or gel aerosolizable material and a solid aerosolizable material. The solid aerosolizable material may comprise, for example, tobacco or a non-tobacco product. Meanwhile, in some embodiments, the non-combustible aerosol provision system generates a vapor or aerosol from one or more such aerosolizable materials.

Typically, the non-combustible aerosol provision system may comprise a non-combustible aerosol provision device and an article for use with the non-combustible aerosol provision system. However, it is envisaged that articles which themselves comprise a means for powering an aerosol generating component may themselves form the non-combustible aerosol provision system. In one embodiment, the non-combustible aerosol provision device may comprise a power source and a controller. The power source may be an electric power source or an exothermic power source. In one embodiment, the exothermic power source comprises a carbon substrate, which may be energized so as to distribute power in the form of heat to an aerosolizable material or heat transfer material in proximity to the exothermic power source. In one embodiment, the power source, such as an exothermic power source, is provided in the article so as to form the non-combustible aerosol provision. In one embodiment, the article for use with the non-combustible aerosol provision device may comprise an aerosolizable material.

In some embodiments, the aerosol generating component is a heater capable of interacting with the aerosolizable material so as to release one or more volatiles from the aerosolizable material to form an aerosol. In one embodiment, the aerosol generating component is capable of generating an aerosol from the aerosolizable material without heating. For example, the aerosol generating component may be capable of generating an aerosol from the aerosolizable material without applying heat thereto, for example via one or more of vibrational, mechanical, pressurization, or electrostatic means.

In some embodiments, the aerosolizable material may comprise an active material, an aerosol forming material and optionally one or more functional materials. The active material may comprise nicotine (optionally contained in tobacco or a tobacco derivative) or one or more other non-olfactory physiologically active materials. A non-olfactory physiologically active material is a material, which is included in the aerosolizable material in order to achieve a physiological response other than olfactory perception. The aerosol forming material may comprise one or more of glycerine, glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate. The one or more functional materials may comprise one or more of flavors, carriers, pH regulators, stabilizers, or antioxidants.

In some embodiments, the article for use with the non-combustible aerosol provision device may comprise aerosolizable material or an area for receiving aerosolizable material. In one embodiment, the article for use with the non-combustible aerosol provision device may comprise a mouthpiece. The area for receiving aerosolizable material may be a storage area for storing aerosolizable material. For example, the storage area may be a reservoir. In one embodiment, the area for receiving aerosolizable material may be separate from, or combined with, an aerosol generating area.

Figure 1:
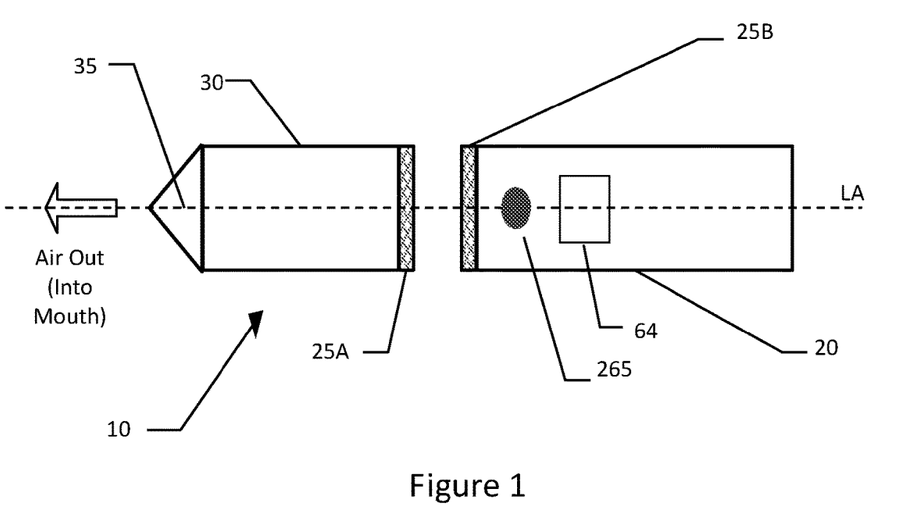
FIG. 1 is a schematic diagram of an electronic aerosol or vapor provision system (EVPS).

Referring now to the drawings, wherein like reference numerals designate identical or corresponding parts throughout the several views, FIG. 1 is a schematic diagram of an electronic vapor/aerosol provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer includes an internal chamber containing a reservoir of a payload such as for example a liquid comprising nicotine, a vaporizer (such as a heater), and a mouthpiece 35. References to 'nicotine' hereafter will be understood to be merely exemplary and can be substituted with any suitable active ingredient. References to 'liquid' as a payload hereafter will be understood to be merely exemplary and can be substituted with any suitable payload such as botanical matter (for example tobacco that is to be heated rather than burned), or a gel comprising an active ingredient or flavoring. The reservoir may be a foam matrix or any other structure for retaining the liquid until such time that it is required to be delivered to the vaporizer. In the case of a liquid or flowing payload, the vaporizer is for vaporizing the liquid, and the cartomizer 30 may further include a wick or similar facility to transport a small amount of liquid from the reservoir to a vaporizing location on or adjacent the vaporizer. In the following, a heater is used as a specific example of a vaporizer. However, it will be appreciated that other forms of vaporizer (for example, those which utilize ultrasonic waves) could also be used and it will also be appreciated that the type of vaporizer used may also depend on the type of payload to be vaporized.

The body 20 includes a re-chargeable cell or battery to provide power to the e-cigarette 10 and a circuit board for generally controlling the e-cigarette. When the heater receives power from the battery, as controlled by the circuit board, the heater vaporizes the liquid and this vapor is then inhaled by a user through the mouthpiece 35. In some specific embodiments the body is further provided with a manual activation device 265, e.g., a button, switch, or touch sensor located on the outside of the body.

The body 20 and cartomizer 30 may be detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector 25B on the body 20 that is used to connect to the cartomizer 30 also serves as a socket for connecting a charging device (not shown) when the body 20 is detached from the cartomizer 30. The other end of the charging device may be plugged into a USB socket to re-charge the cell in the body 20 of the e-cigarette 10. In other implementations, a cable may be provided for direct connection between the electrical connector 25B on the body 20 and a USB socket.

The e-cigarette 10 is provided with one or more holes (not shown in FIG. 1) for air inlets. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. When the heater is activated to vaporize the nicotine from the cartridge, the airflow passes through, and combines with, the generated vapor, and this combination of airflow and generated vapor then passes out of the mouthpiece 35 to be inhaled by a user. Except in single-use devices, the cartomizer 30 may be detached from the body 20 and disposed of when the supply of liquid is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the liquid reservoir and mouthpiece (which can be replaced when the liquid from the reservoir is exhausted), and a vaporizer comprising a heater (which is generally retained). As another example, the charging facility may connect to an additional or alternative power source, such as a car cigarette lighter.

Figure 2:
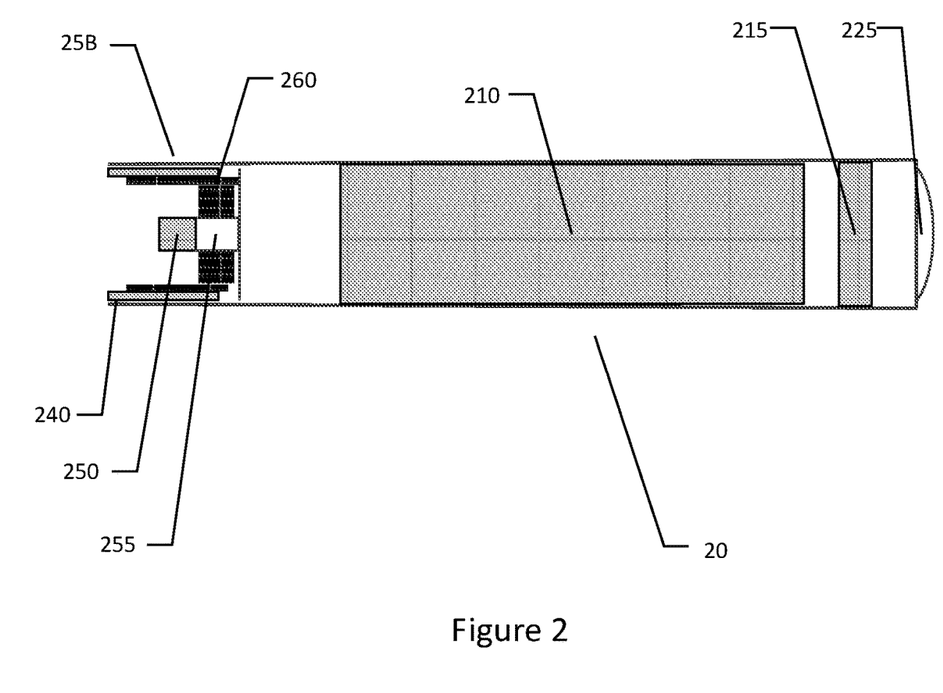
FIG. 2 is a schematic diagram of the body of the EVPS of FIG. 1.

FIG. 2 is a schematic (simplified) diagram of the body 20 of the e-cigarette 10 of FIG. 1 in accordance with some embodiments of the disclosure. FIG. 2 can generally be regarded as a cross-section in a plane through the longitudinal axis LA of the e-cigarette 10. Note that various components and details of the body, e.g., such as wiring and more complex shaping, have been omitted from FIG. 2 for reasons of clarity.

The body 20 includes a battery or cell 210 for powering the e-cigarette 10 in response to a user activation of the device. Additionally, the body 20 includes a control unit (not shown in FIG. 2), for example a chip such as an application specific integrated circuit (ASIC) or microcontroller, for controlling the e-cigarette 10. The microcontroller or ASIC includes a CPU or micro-processor. The operations of the CPU and other electronic components are generally controlled at least in part by software programs running on the CPU (or other component). Such software programs may be stored in non-volatile memory, such as ROM, which can be integrated into the microcontroller itself, or provided as a separate component. The CPU may access the ROM to load and execute individual software programs as and when required. The microcontroller also contains appropriate communications interfaces (and control software) for communicating as appropriate with other devices in the body 10.

The body 20 further includes a cap 225 to seal and protect the far (distal) end of the e-cigarette 10. Typically there is an air inlet hole provided in or adjacent to the cap 225 to allow air to enter the body 20 when a user inhales on the mouthpiece 35. The control unit or ASIC may be positioned alongside or at one end of the battery 210. In some embodiments, the ASIC is attached to a sensor unit 215 to detect an inhalation on mouthpiece 35 (or alternatively the sensor unit 215 may be provided on the ASIC itself). An air path is provided from the air inlet through the e-cigarette, past the airflow sensor 215 and the heater (in the vaporizer or cartomizer 30), to the mouthpiece 35. Thus, when a user inhales on the mouthpiece of the e-cigarette, the CPU detects such inhalation based on information from the airflow sensor 215.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, e.g., in a direction parallel to (co-aligned with) the longitudinal axis LA. In view of the resilient nature of the spring 255, this compression biases the spring 255 to expand, which has the effect of pushing the electrical contact 250 firmly against connector 25A of the cartomizer 30, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

As mentioned above, a button 265, which represents a form of manual activation device 265, may be located on the outer housing of the body 20. The button 265 may be implemented using any appropriate mechanism which is operable to be manually activated by the user—for example, as a mechanical button or switch, a capacitive or resistive touch sensor, and so on. It will also be appreciated that the manual activation device 265 may be located on the outer housing of the cartomizer 30, rather than the outer housing of the body 20, in which case, the manual activation device 265 may be attached to the ASIC via the connections 25A, 25B. The button 265 might also be located at the end of the body 20, in place of (or in addition to) cap 225.

Figure 3:
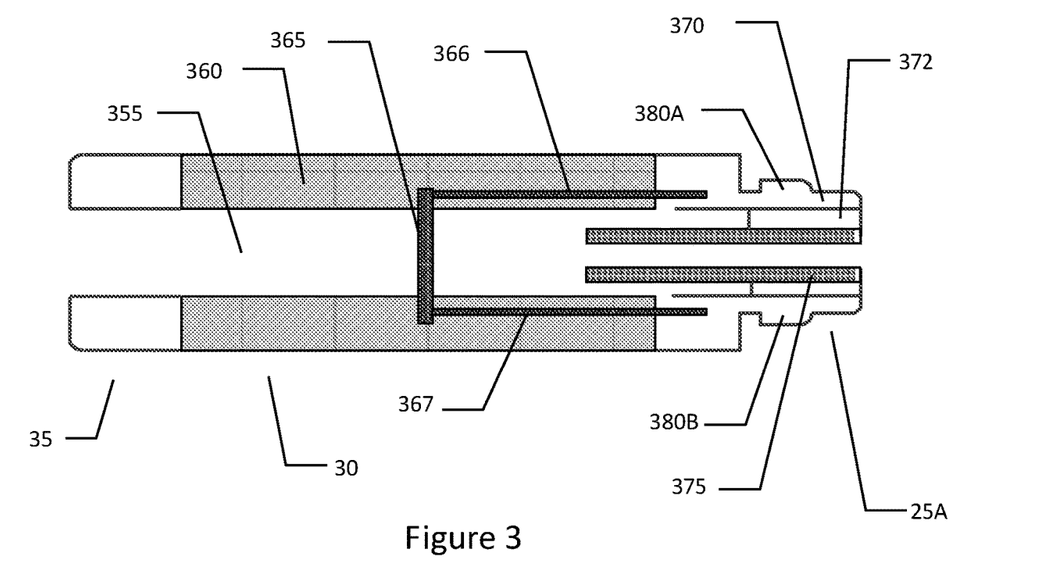
FIG. 3 is a schematic diagram of the cartomizer of the EVPS of FIG. 1.

FIG. 3 is a schematic diagram of the cartomizer 30 of the e-cigarette 10 of FIG. 1 in accordance with some embodiments of the disclosure. FIG. 3 can generally be regarded as a cross-section in a plane through the longitudinal axis LA of the e-cigarette 10. Note that various components and details of the cartomizer 30, such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of liquid 360 is provided around the air passage 335. This reservoir 360 may be implemented, for example, by providing cotton or foam soaked in liquid. In other implementations, the reservoir 360 may be implemented as a hollow space within the cartomizer 30 in which liquid is held (and generally free to move around the hollow space). The cartomizer 30 also includes a heater 365 for heating liquid from reservoir 360 to generate vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 of the main body 20 via connector 25A (the details of the wiring between the power lines 366 and 367 and connector 25A are omitted from FIG. 3).

The connector 25A includes an inner electrode 375, which may be silver-plated or made of some other suitable metal or conducting material. When the cartomizer 30 is connected to the body 20, the inner electrode 375 contacts the electrical contact 250 of the body 20 to provide a first electrical path between the cartomizer 30 and the body 20. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body 20 to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette 10. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer and body are held in a fixed position relative to one another, with minimal wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
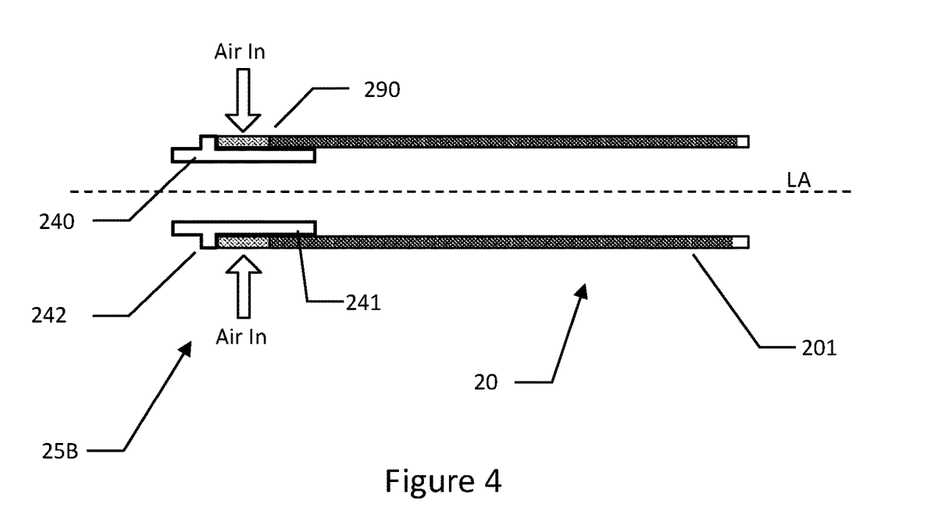
FIG. 4 is a schematic diagram of the external housing of the body with details of the connector of the EVPS of FIG. 1.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar. The external housing 201 may also comprise the manual activation device 265 (not shown in FIG. 4) so that the manual activation device 265 is easily accessible to the user.

The body connector 240 extends from this external housing 201 of the body 20. The body connector 240 as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body, which together prevent movement of the collar 290 in an axial direction (e.g., parallel to axis LA). However, collar 290 is free to rotate around the shaft portion 241 (and hence also axis LA).

As mentioned above, the cap 225 is provided with an air inlet hole to allow air to flow when a user inhales on the mouthpiece 35. However, in some embodiments the majority of air that enters the device when a user inhales flows through collar 290 and body connector 240 as indicated by the two arrows in FIG. 4.

Referring again to FIG. 1, in an embodiment of the disclosure an aerosol provision system 10 is configured to generate aerosol from an aerosol generating material for user inhalation. As noted previously herein, the aerosol generating material may comprise any suitable liquid or gel that may be vaporized or aerosolized using a heater or other means (such as an ultrasonic transducer), or a botanical that is to be heated to release a vapor or aerosolized particles.

Figure 6:
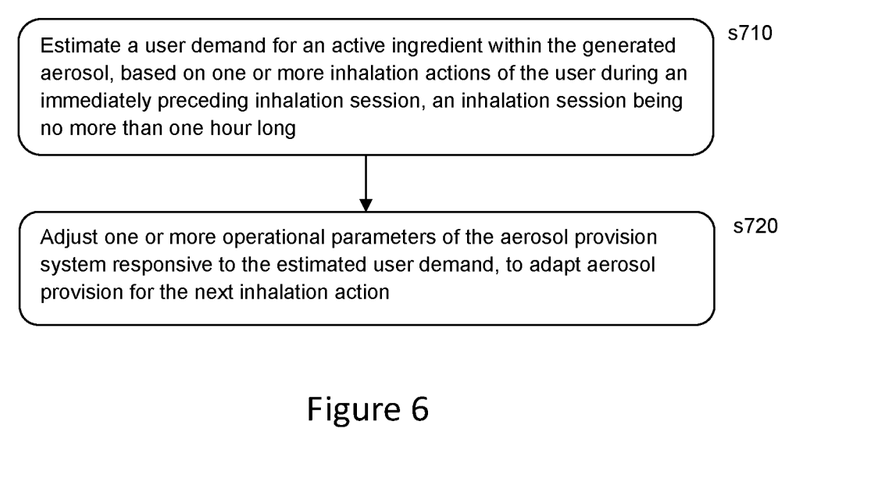
FIG. 6 is a flowchart for an aerosol provision method.

Referring also to FIG. 6, the aerosol provision system may either comprise an EVPS 10 alone, or may be a combination of an EVPS and a remote device operable to communicate with the EVPS, such as a mobile phone 100 communicating via a local wireless protocol such as Bluetooth®, or in principle a remote server if the EVPS is operable to directly or indirectly access the internet (e.g., using WiFi®).

The aerosol provision system comprises a computer, for example, a processor 64 of the EVPS or a processor of the phone or server (or any combination thereof), configured firstly to estimate a user demand for an active ingredient within the generated aerosol, based on one or more inhalation actions of the user during an immediately preceding inhalation session, an inhalation session being no more than one hour long, and configured secondly to adjust one or more operational parameters of the aerosol provision system responsive to the estimated user demand, to adapt aerosol provision for the next inhalation action.

Estimation of the user demand is described in more detail later herein.

In the case where some or all of the computer operations occur on a mobile phone or server, the resulting estimate and/or adjustments, as appropriate, are transmitted back to the EVPS.

In this way, the aerosol provision system can predict the behavior of the user based on short term behavior (where here 'short term' means, for example, less than one hour).

In an embodiment of the present disclosure, an inhalation session corresponds to a sequence of inhalations. The sequence may correspond to a characteristic pattern. Hence, in this case an inhalation session may comprise a characteristic sequence, such as a high-to-low volume sequence of puffs. Such a sequence may be characteristic of a user wishing to receive a strong effect from inhalation initially, but then having a less strong wish as the effects are felt, until the inhalations taper off as the user is sated. Alternatively, an inhalation session may correspond to a predetermined number, or range, of inhalations on the EVPS by the user. For example, a session may be defined as 10 inhalations or between 8 to 12 inhalations. Additionally, or alternatively, a session may be defined by a predefined time from an initial inhalation on the EVPS by the user. For example, the predetermined time may be four minutes. Hence, a session can be defined when the total number of inhalations reaches 8 to 12 inhalations or when the time elapsed from the first inhalation reaches four minutes. It should be appreciated that the values for the predetermined number of inhalations and predetermined time have been given purely as an example, and other numbers and times may be used in other implementations as appropriate.

Alternatively or in addition, in an embodiment of the present disclosure an inhalation session corresponds to a sequence of inhalations, the sequence separated from another session by a pause of more than a threshold duration. The threshold duration may be selected for ease of comprehension by the user (e.g., 5, 10, 15, 20, 25, 30, 35, 40, 45, 50, or 55 minutes, or a period in the range 5-45 minutes, or a period in the range 10-30 minutes, or a period in the range 15-20 minutes), or it may be selected on a pharmokinetic basis, such as the so-called half-life of nicotine in the body (approximately 2 hours) or a physiological basis, such as a perceived drop in brain stimulation by the nicotine (for example in the order of 15-25 minutes, averaging around 18-20 minutes). Optionally this half-life may in turn be individualized, e.g., on the basis of sex, build (size, weight etc), ethnicity and the like. A look-up table of half-life values, or a scaling value for one or more physiological factors of the user may be used to refine an otherwise generic half-life value.

Hence an inhalation session may comprise a characteristic pattern or may be separated from another session by a threshold duration of non-use.

Where the user 'grazes', which is to say, inhales in a similar and ongoing manner on the EVPS at relatively frequent intervals that are shorter than the threshold duration, then the inhalation session may simply time out as being an hour long (e.g., the previous hour), rather than being characterized by either of the above criteria. It will be appreciated that where a session is simply based on series of inhalations over a preceding period, it need not be an hour long, but may be any suitable period, such as 45, 30, or 15 minutes (although shorter periods may reduce the accuracy of any prediction due to fewer sample inhalation events).

The user demand for an active ingredient within the generated aerosol may be estimated on a per-puff basis (e.g., for the next inhalation action), or for the next puff session (for example predicting the characteristic pattern and varying active ingredient delivery accordingly), based on the recent short term mood or behavior of the user as indicated through the proxy of recent inhalation actions (e.g., within a preceding characteristic sequence, or within a preceding period of up to an hour).

Hence, in an embodiment of the present disclosure, then based on one or more inhalation actions of the user during an immediately preceding inhalation session, the user demand may then be estimated for a next inhalation or inhalation session by the user.

The estimated user demand for a next inhalation or inhalation session by the user may be based on any suitable property, or combination of properties, of the one or more inhalation actions during the immediately preceding inhalation session. For example, the property may be a property associated with an individual inhalation, such as the inhalation strength, the duration, or the inhalation strength as a function of time. In examples where a plurality of inhalations is used to estimate the user demand, an average or cumulative measure for the one or more properties of the immediately preceding inhalation session may be used.

In embodiments, in response to at least a first inhalation action of the user during an immediately preceding inhalation session that causes more than a threshold amount of aerosol to be generated, the computer is configured to estimate an increased user demand for the next inhalation by the user based upon the at least first inhalation.

The threshold amount is set to be indicative of a heightened demand for the active ingredient. In a first instance, the threshold may be a default amount, which may be fixed or itself may be the result of a separate process or analysis of use—for example, the threshold may vary during the day, or may vary over a fixed cycle triggered by initialization of an inhalation session. The threshold may also vary depending on the internal state of the device (for example rising if the power or active ingredient resources are running low, to reduce the chance of triggering a heightened response so as to prolong delivery), or information about the active ingredient (for example if a reservoir changes, or if there is a control for flow rate or the like on the device that alter delivery properties of the device). Similarly, the threshold may vary according to a vaping cessation program or vaping limiting or capping option or similar, selected by the user.

In a second instance, alternatively or in addition to any of the above considerations, the threshold may be responsive to the characteristic pattern of an inhalation session, for example being higher at the start of the session and lower at the end, reflecting the above-mentioned likely change in demand over the course of the session and hence reflecting differences in what will constitute a heightened demand compared to the normal characteristic pattern of the session itself.

In this latter case, a device may learn and store for comparison one or more characteristic inhalation session patterns of the user over any period of time, even if the current prediction itself is only based on user inhalation behavior during the most recent inhalation session, or proceeding hour.

Hence, in this latter case, in response to a first inhalation action of the user at a first point in an immediately preceding inhalation session that caused more than a threshold amount of aerosol to be generated, the first point in the preceding inhalation session corresponding to a next inhalation by the user in the current inhalation session, the computer maybe configured to estimate an increased user demand for the next inhalation by the user based upon the first inhalation.

Conversely, the user's recent inhalation behavior may indicate a less than expected demand for the active ingredient, rather than a heightened demand. Hence in response to at least a first inhalation action of the user during an immediately preceding inhalation session causing less than a (second) threshold amount of aerosol to be generated, the computer is configured to estimate a reduced user demand for the next inhalation by the user based upon the at least first inhalation.

In a similar manner to the heightened demand above, such a threshold may be a default or the result of a separate user option, strategy or analysis, or may vary as a function of expected position within a characteristic pattern of an inhalation session.

In any of the above scenarios, and may be in response to an estimated user demand for a next inhalation, the computer is configured to generate aerosol meeting the estimated user demand within a predetermined inhalation profile. In other words, the EVPS should attempt to deliver the desired active ingredient during the course of a normal puff action on the part of the user, such that the user does not need to inhale for noticeably longer or shorter or more deeply or more shallowly than they would do otherwise.

This may be achieved for example by increasing or decreasing the temperature of the heater to deliver more or less vapor or aerosol, or increasing or restricting airflow to deliver more or less vapor or aerosol, or increasing or restricting the interaction of the payload with the heater to deliver more or less vapor or aerosol. Other techniques may be apparent to the skilled person.

What constitutes a normal puff action on the part of the user in terms of duration and depth or rate of inhalation may be separately predicted. To a first approximation, it may simply be a default period, for example based on empirical studies of average inhalation duration. In this case if demand judged on a per-delivery basis then in effect the inhalation duration is not taken into account, as it is not predicted to vary (even if in practice it does).

To a second approximation and maybe an average period based on empirical measurements of the individual user again potentially therefore the duration is effectively not taking into account if it is considered constant, although the thresholds themselves will implicitly take the user's average duration into account, as these will reflect deviations from normal levels of delivery per inhalation.

Meanwhile to a third approximation it may be based upon one or more of recent inhalation actions or historical inhalation behavior of the user relating to factors such as time of day, location and the like.

In any event, given predicted demand and optionally a predicted inhalation duration, one or more operational parameters of the aerosol provision system such as those described above may be adjusted in response, to adapt their aerosol provision for the next inhalation action.

As noted previously, alternatively or in addition to the next individual puff, in embodiments of the present disclosure the user demand may be estimated for at least part of a next inhalation session by the user, where part of a next inhalation session means some or all of such a session, and comprises two or more puffs in sequence.

In this scenario, in an embodiment of the disclosure then in response to at least a first inhalation action of the user during an immediately preceding inhalation session causing more than a threshold amount of aerosol to be generated, the computer is configured to estimate an increased user demand for at least part of the next inhalation session based upon the at least first inhalation.

Hence, alternatively or in addition to predicting increased demand for an individual puff, where the previous session contained one or puffs indicating dissatisfaction with the default delivery (for example by exceeding an upper threshold on one or puffs as described previously herein), then computer may modify a baseline level of delivery for the whole arc of the next session, of which the next inhalation action is a part. For example, the amount of active ingredient delivered per puff within inhalation session may be increased by 5% for each puff in response to a single puff in a previous session exceeding a threshold, or may be increased by 10% for each puff in response to two puffs in a previous session exceeding a threshold. The relationship between behavior in the previous session and modification of the current session may take any suitable form. For example, the position within the preceding inhalation sequence of the one or puffs exceeding a threshold may indicate a peak in a graduated modification to the delivery of additional active ingredient within the next inhalation sequence of which the next inhalation action is part.

Hence as a non-limiting example, in a hypothetical 10 puff sequence where previously the user inhales more than a threshold amount during puffs 6 and 7, the resulting percent increase in aerosol delivery for the next sequence of inhalations may take the form: +0, +0, +1, +3, +5, +10, +10, +5, +3, +1. The actual changes in value may for example be determined empirically, for example based upon a perceived level of effect as a function of the amount of active ingredient taken into the body, and may be relative to the default amount per puff in the sequence (e.g., a percentage increase), or may be absolute (e.g., a separate fixed or variable increase).

Similarly, alternatively or in addition to predicting increased demand for an individual puff, in response to a first sequence of inhalation actions of the user during at least a first part of an immediately preceding inhalation session that caused more than a combined threshold amount of aerosol to be generated, the first part in the preceding inhalation session substantially corresponding to a next part in the current inhalation session, then the computer may be configured to estimate a pattern of user demand for at least part of the next sequence of inhalations by the user based upon the first sequence.

In other words, the above principles of generating a graduated modification to the delivery of additional active ingredient within the next inhalation sequence may also be applied to cumulative demand over some or all of the preceding sequence, rather than an indication of high demand for one or more individual puffs. Hence one or cumulative thresholds may be used to determine whether for example the user demands more or less active ingredient from a first part of an inhalation session sequence as a whole, or similarly more or less active ingredient from a middle part of an inhalation session sequence, or similarly more or less active ingredient from an end part of an inhalation session sequence, and modify the delivery of active ingredient during the upcoming inhalation session accordingly.

In embodiments where the prediction of behavior over the course of an upcoming session may contribute to modification of the aerosol delivery for current and future inhalation actions, then the characteristic pattern of the current inhalation session may need to be predicted.

In a similar manner to individual puffs, to a first approximation this may take the form of a default pattern, optionally based on empirical measurements by the manufacturer of the device. To a second approximation, it may take the form of a default pattern learned from the individual user of this device, for example by generating an inhalation envelope over the course of successive sessions, where sessions may be separated by a minimum period, as described previously herein, by measuring inhalation levels on a per inhalation action basis and averaging over the course of multiple sessions during ongoing use of the device.

To a third approximation, a plurality of such inhalation envelopes may be developed, for example using a clustering algorithm to identify different classes of inhalation envelope based on data captured by the EVPS. Such processing may be performed for example by a remote mobile phone or server directly or indirectly in communication with the EVPS. Such inhalation envelopes may then be associated with other circumstantial data such as time of day or the location of the user, or any other data indicative of the behavior of the user, to determine any correlation between the circumstantial data and individual inhalation envelopes, to predict the most likely next inhalation envelope and hence characteristic pattern of the next inhalation session. Alternatively and in addition, as the next inhalation session progresses, it may be compared with a plurality of such inhalation envelopes to find the closest match upon which to base predictions; as such modifications to inhalation actions may move and refine from a default model to a characteristic model or to a succession of increasingly characteristic models as the characteristic nature of the current inhalation session becomes apparent.

Again as with individual puffs, in addition to demanding more active ingredient, optionally the user may wish for less and hence in addition to exceeding individual or cumulative thresholds as described above, the user may inhale less than a lower individual or cumulative threshold.

Hence, in response to at least a first inhalation action of the user during an immediately preceding inhalation session causing less than a threshold amount of aerosol to be generated, the computer may be configured to estimate a reduced user demand for at least part of the next inhalation session based upon the at least first inhalation.

Again, the above techniques relating to how modifications may relate to individual corresponding puffs or may be graduated over a modification curve within oral part of an inhalation session may apply to reducing the production of active ingredient in a similar manner to increasing it.

Again as with individual puffs, it is desirable for the modification of the generation of active ingredient to meet predicted user demand to enable this modification to occur during a normal inhalation session. That is to say that the user should not need to inhale more frequently or more often within a session in order to receive the predicted change in amount of active ingredient. Accordingly, in response to an estimated user demand for at least part of the next sequence of inhalations, the computer may be configured to generate aerosol meeting the estimated user demand within some or all of a predetermined sequence. As mentioned above, this may be achieved by modifying an inhalation envelope such that the integral of that envelope is increased or decreased by the desired amount, either over the whole globe, or optionally within a subsection of it, such as the beginning, middle or end as described previously herein.

Whilst the above described examples refer to estimates, predictions, and thresholds representative of user demand as a function of inhalation actions or sequences (whether frequency, duration, volume, intensity, or any combination thereof), alternatively or in addition any or all of the estimates, predictions and thresholds may be responsive to the blood concentration of the active ingredient in the user estimated to arise from one or more inhalation actions of the user during an immediately preceding inhalation session.

In other words, the blood concentration of the active ingredient, either on a momentary basis responsive to a single puff or as part of an envelope shaped by an inhalation sequence, may be inferred from the puffs themselves using known or empirically determined pharmokinetic relationships, based for example on the inhalation whether frequency, duration, volume, intensity, or any combination thereof, and optionally also the concentration of the active ingredient in the payload (where this is variable), and also optionally physiological details of the user (such as height, weight, gender, and the like). This may then be used alongside or instead of the puffs themselves to estimate the user demand for an active ingredient within the generated aerosol, based on the blood concentration levels estimated from one or more inhalation actions of the user during an immediately preceding inhalation session.

Hence, also an adjustment of one or more operational parameters of the aerosol provision system, responsive to the estimated user demand, may be responsive to an estimate of the current blood concentration of the active ingredient in the user.

In the above cases, it will be appreciated that sometimes the active ingredient itself is not what gives the desired subjective effect, but one or more metabolites, or secondary compounds released in response the presence of the active ingredient or a metabolite. Hence, the above references to the active ingredient can encompass these metabolites or secondary compounds as appropriate.

Although the above describes scenarios where the computer is configured to estimate an increased or decreased user demand for the next inhalation or inhalations based upon the at least a first inhalation action of the user during an immediately preceding inhalation session that causes more or less than a threshold amount of aerosol to be generated, it should be appreciate that other properties of the at least a first inhalation action of the user during an immediately preceding inhalation session may be indicative of an increased or decreased user demand. For example, if the at least a first inhalation exceeds a certain first length of time from the moment of inhalation to the end of the inhalation, this may signify an increased user demand. Conversely, if the at least a first inhalation is below a certain second length of time from the moment of inhalation to the end of the inhalation (which may be shorter than the first length of time), this may signify a decreased user demand. Equally, if the at least first inhalation exceeds a certain first pressure threshold (which may signify the strength of the inhalation), this may signify an increased user demand. Conversely, if the at least a first inhalation is below a certain second pressure threshold (which may be lower than the first pressure threshold), this may signify a decreased user demand. Equally, combinations of parameters may be used to estimate a user demand.

In other examples, the estimated user demand may be based on properties that characterize a plurality of inhalations, for example the time between successive inhalations or the frequency of inhalations. These properties may also be used to estimate an increase or decrease in user demand based on exceeding or falling below one or more thresholds.

Additionally, the estimated user demand may be based on an average measure of properties associated with a plurality of inhalation actions during the immediately preceding inhalation session. For example, the estimated user demand may be based on an average of the inhalation strength or duration.

Referring again to FIG. 1, the EVPS may be a self-contained unit (commonly referred to as an e-cigarette, even if the device itself does not necessarily conform to the shape or dimensions of a conventional cigarette). Such an e-cigarette may comprise an airflow measuring means, a processing means and optionally one or more feedback means such as haptic, audio or light or display means.

Figure 5:
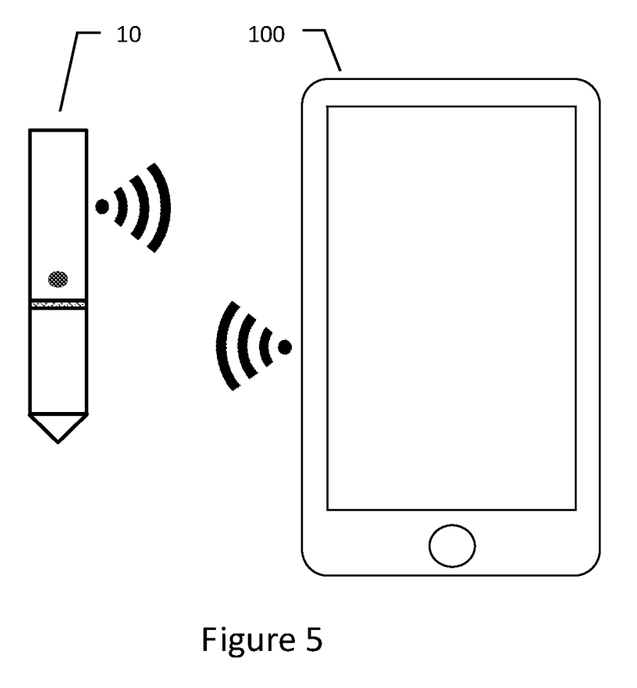
FIG. 5 is an illustration of a system comprising the EVPS and a remote device.

Alternatively, referring to FIG. 5, an EVPS system may comprise two components, such as an e-cigarette 10 and a mobile phone or similar device (such as a tablet) 100 operable to communicate with the e-cigarette (for example to at least receive data from the e-cigarette), for example via Bluetooth®.

The mobile phone may then comprise the processing means and one or more feedback means such as haptic, audio or light or display means, alternatively or in addition to those of the e-cigarette.

Optionally an EVPS system may comprise an e-cigarette 10 operable to communicate with a mobile phone 100, in which the mobile phone stores one or more parameters or other data (such as data characteristic of one or more aspects of usage by the user) for the EVPS, and receives such parameters or data from the e-cigarette. The phone may then optionally perform processing on such parameters or data and either return processed data or instructions to the EVPS, display a result to the user (or perform another action) or forward processed or unprocessed parameters or data on to a remote server.

Optionally the mobile phone or the EVPS itself may be operable to wirelessly access data associated with an account of the user at such a remote server.

Hence the operations of the computer may be located within one or more selected from the list consisting of the aerosol generating unit itself, a remote server operable to communicate with the aerosol provision system, a mobile computing device operable to communicate with the aerosol provision system, and a remote server operable to communicate with a mobile computing device operable to communicate with the aerosol provision system.

Referring now to FIG. 6, an aerosol provision method for an aerosol provision system configured to generate aerosol from an aerosol generating material for user inhalation comprises:

In a step s710, estimating a user demand for an active ingredient within the generated aerosol, based on one or more inhalation actions of the user during an immediately preceding inhalation session, an inhalation session being no more than one hour long.

In a step s720, adjusting one or more operational parameters of the aerosol provision system responsive to the estimated user demand, to adapt aerosol provision for the next inhalation action.

It will be apparent to a person skilled in the art that variations in the above method corresponding to operation of the various embodiments of the method or apparatus as described and claimed herein are considered within the scope of the present disclosure, including but not limited to:

- an inhalation session corresponding to one selected from the list consisting of a sequence of inhalations, the sequence corresponding to a characteristic pattern, and a sequence of inhalations, the sequence separated from another session by a pause of more than a threshold duration;
- the user demand being estimated for a next inhalation by the user;
- in response to a property of at least a first inhalation action of the user during an immediately preceding inhalation session surpassing a threshold, estimating an increased user demand for the next inhalation by the user based upon the at least first inhalation;
- in response to at least a first inhalation action of the user during an immediately preceding inhalation session causing more than a threshold amount of aerosol to be generated, estimating an increased user demand for the next inhalation by the user based upon the at least first inhalation;
    - in either case, where a property or amount of aerosol has passed a threshold, the property or aerosol may be a proxy for the amount of active ingredient inhaled. In a system where the amount of active ingredient per unit volume of aerosol is variable (e.g., by the user), the threshold may be adjusted responsive to the current concentration of active ingredient in the aerosol.
- in response to a first inhalation action of the user at a first point in an immediately preceding inhalation session that caused more than a threshold amount of aerosol to be generated, the first point in the preceding inhalation session corresponding to a next inhalation by the user in the current inhalation session, estimating an increased user demand for the next inhalation by the user based upon the first inhalation;
- in response to a property of at least a first inhalation action of the user during an immediately preceding inhalation session being less than a second threshold, estimating a reduced user demand for the next inhalation by the user based upon the at least first inhalation;
- in response to at least a first inhalation action of the user during an immediately preceding inhalation session causing less than a threshold amount of aerosol to be generated, estimating a reduced user demand for the next inhalation by the user based upon the at least first inhalation.
- in response to an estimated user demand for a next inhalation, generating aerosol meeting the estimated user demand within a predetermined inhalation profile;
- the user demand being estimated for at least part of a next inhalation session by the user;
- in response to a property of at least a first inhalation action of the user during an immediately preceding inhalation surpassing a threshold, estimating an increased user demand for at least part of the next inhalation session based upon the at least first inhalation;
- in response to at least a first inhalation action of the user during an immediately preceding inhalation session causing more than a threshold amount of aerosol to be generated, estimating an increased user demand for at least part of the next inhalation session based upon the at least first inhalation;
- in response to a first sequence of inhalation actions of the user during at least a first part of an immediately preceding inhalation session that caused more than a combined threshold amount of aerosol to be generated, the first part in the preceding inhalation session corresponding to a next part in the current inhalation session, estimating a pattern of user demand for at least part of the next sequence of inhalations by the user based upon the first sequence;
- in response to a property of at least a first inhalation action of the user during an immediately preceding inhalation session being less than a second threshold, estimating a reduced user demand for the next inhalation by the user based upon the at least first inhalation;
- in response to at least a first inhalation action of the user during an immediately preceding inhalation session causing less than a threshold amount of aerosol to be generated, estimating a reduced user demand for at least part of the next inhalation session based upon the at least first inhalation;
- in response to an estimated user demand for at least part of the next sequence of inhalations, generating aerosol meeting the estimated user demand within a some or all of predetermined sequence;
- an estimate of a user demand for an active ingredient being responsive to the blood concentration of the active ingredient in the user estimated to arise from one or more inhalation actions of the user during an immediately preceding inhalation session;
- an adjustment of one or more operational parameters of the aerosol provision system responsive to the estimated user demand being responsive to an estimate of the current blood concentration of the active ingredient in the user;

an adjustment of one or more operational parameters of the aerosol provision system responsive to the estimated user demand being responsive to a limit on the current blood concentration of the active ingredient in the user; and some or all of the estimating operations being located within one or more selected from the list consisting of the aerosol generating unit, a remote server operable to communicate with the aerosol provision system, a mobile computing device operable to communicate with the aerosol provision system, and a remote server operable to communicate with a mobile computing device operable to communicate with the aerosol provision system.

It will be appreciated that the above methods may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a non-transitory machine-readable medium such as a floppy disk, optical disk, hard disk, solid state disk, PROM, RAM, flash memory, or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these or other networks.

In a variant embodiment of the disclosure, a first EVPS of a user may communicate some or all of its user settings to another EVPS. The user settings may comprise settings related to an implementation of the above disclosed methods, such as data characteristic of user behavior, and/or data relating to modification of the EVPS operation.

Such data may be relayed between devices either directly (e.g. via a Bluetooth® or near-field communication) or via one or more intermediary devices, such as a mobile phone owned by the user of the two devices or a server on which the user has an account linking the two devices.

In this way, a user may easily share the data from one device to another, for example if the user has two EVPS devices, or if the user wishes to replace one EVPS device with another without losing accumulated personalization data.

Optionally in this embodiment, where the second EVPS differs in type from the first EVPS (for example by having a different default power level, or heating efficiency), then a conversion factor or look-up table for converting operational parameters from the first EVPS to the second EVPS may be employed. This may be provided in software or firmware of the second EVPS, and identify the first EVPS and hence the appropriate conversions when making direct communication (or where data is relayed without change via an intermediary such as a phone). Alternatively or in addition an app on the phone may provide the conversion, optionally downloading the relevant conversions in response to the identity of the first and second EVPS. Again, alternatively or in addition a remote server may provide the conversion, in response to the identity of the first and second EVPS as associated with a user's account.

The foregoing discussion discloses and describes merely exemplary embodiments of the present disclosure. As will be understood by those skilled in the art, the present disclosure may be embodied in other specific forms without departing from the essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. An aerosol provision system configured to generate aerosol from an aerosol generating material for user inhalation, the system comprising:
   a computer configured to:
      estimate an increased user demand for an active ingredient within a generated aerosol for a next inhalation action by the user, based on one or more inhalation actions of the user during an immediately preceding inhalation session, an inhalation session being no more than one hour long, wherein the increased user demand is estimated in response to a property of at least a first inhalation action of the user during the immediately preceding inhalation session surpassing a threshold; and
      adjust one or more operational parameters of the aerosol provision system responsive to the estimated user demand, to adapt aerosol provision for a next inhalation action.

2. The aerosol provision system of claim 1, wherein the inhalation session corresponds to a sequence of inhalations, the sequence corresponding to a characteristic pattern.

3. The aerosol provision system of claim 1, wherein the inhalation session corresponds to a sequence of inhalations, the sequence separated from another session by a pause of more than a threshold duration.

4. The aerosol provision system of claim 1, wherein the property of the at least first inhalation action is an amount of aerosol generated in response to the at least a first inhalation action of the user during the immediately preceding inhalation session, and
   wherein the threshold is a threshold amount of aerosol.

5. The aerosol provision system of claim 1, wherein the property of the at least first inhalation action is an amount of aerosol generated in response to the first inhalation action of the user at a first point in the immediately preceding inhalation session, and
   wherein the threshold is a threshold amount of aerosol to be generated;
   at the first point in the preceding inhalation session, which corresponds to a next inhalation by the user in the current inhalation session.

6. The aerosol provision system of claim 1, wherein, in response to the property of the at least a first inhalation action of the user during the immediately preceding inhalation session being less than a second threshold,
   the computer is configured to estimate a reduced user demand for the next inhalation action by the user based upon the at least first inhalation action.

7. The aerosol provision system of claim 1, wherein, in response to at least the first inhalation action of the user during the immediately preceding inhalation session causing less than a second threshold amount of aerosol to be generated, the computer is configured to estimate a reduced user demand for the next inhalation action by the user based upon the at least first inhalation action.

8. The aerosol provision system of claim 1, wherein in response to the estimated user demand for the next inhalation action,
the computer is configured to generate aerosol meeting the estimated user demand within a predetermined inhalation profile.

9. An aerosol provision system configured to generate aerosol from an aerosol generating material for user inhalation, the system comprising:
a computer configured to:
estimate an increased user demand for an active ingredient within a generated aerosol for a next inhalation action by the user, based on one or more inhalation actions of the user during an immediately preceding inhalation session, an inhalation session being no more than one hour long; and
adjust one or more operational parameters of the aerosol provision system responsive to the estimated user demand, to adapt aerosol provision for a next inhalation action, wherein the threshold is adjustable in response to a concentration of the active ingredient in the aerosol.

10. The aerosol provision system of claim 1, wherein the user demand is additionally estimated for at least part of a next inhalation session by the user.

11. The aerosol provision system of claim 10, wherein the computer is configured to estimate an increased user demand for at least part of the next inhalation session based upon the at least first inhalation action.

12. The aerosol provision system of claim 10, wherein the computer is configured to estimate the increased user demand for at least part of the next inhalation session based upon the at least first inhalation action.

13. The aerosol provision system of claim 10, wherein in response to a first sequence of inhalations actions of the user during at least a first part of the immediately preceding inhalation session causing more than a combined threshold amount of aerosol to be generated, the first part in the preceding inhalation session corresponding to a next part in a current inhalation session,
the computer is configured to estimate a pattern of user demand for at least part of a next sequence of inhalations by the user based upon the first sequence of inhalations.

14. The aerosol provision system of claim 10, wherein in response to the property of the at least a first inhalation action of the user during the immediately preceding inhalation session, falling below a second threshold,
the computer is configured to estimate a reduced user demand for at least part of the next inhalation session based upon the at least first inhalation action.

15. The aerosol provision system of claim 10, wherein in response to the at least the first inhalation action of the user during the immediately preceding inhalation session causing less than a second threshold amount of aerosol to be generated,
the computer is configured to estimate a reduced user demand for at least part of the next inhalation session based upon the at least first inhalation action.

16. The aerosol provision system of claim 10, wherein in response to an estimated user demand for at least part of a next sequence of inhalations,
the computer is configured to generate aerosol meeting the estimated user demand within some or all of a predetermined sequence.

17. The aerosol provision system of claim 10, wherein the threshold is adjustable in response to a concentration of the active ingredient in the aerosol.

18. The aerosol provision system of claim 1, wherein the estimate of the increased user demand for the active ingredient is responsive to a blood concentration of the active ingredient in the user estimated to arise from one or more inhalation actions of the user during the immediately preceding inhalation session.

19. The aerosol provision system of claim 1, wherein an adjustment of one or more operational parameters of the aerosol provision system responsive to the estimated user demand is responsive to an estimate of a current blood concentration of an active ingredient in the user.

20. The aerosol provision system of claim 19, wherein the adjustment of one or more operational parameters of the aerosol provision system responsive to the estimated user demand is responsive to a limit on the current blood concentration of the active ingredient in the user.

21. The aerosol provision system of claim 1, wherein some or all operations of the computer are located within one or more selected from a list consisting of:
  i. an aerosol generating unit;
  ii. a remote server operable to communicate with the aerosol provision system;
  iii. a mobile computing device operable to communicate with the aerosol provision system; and
  iv. a remote server operable to communicate with a mobile computing device operable to communicate with the aerosol provision system.

22. An aerosol provision method for an aerosol provision system configured to generate aerosol from an aerosol generating material for user inhalation, the method comprising the steps of:
estimating an increased user demand for an active ingredient within a generated aerosol for a next inhalation action by the user, based on one or more inhalation actions of a user during an immediately preceding inhalation session, an inhalation session being no more than one hour long, wherein the increased user demand is estimated in response to a property of at least a first inhalation action of the user during the immediately preceding inhalation session surpassing a threshold; and
adjusting one or more operational parameters of the aerosol provision system responsive to the estimated user demand, to adapt aerosol provision for a next inhalation action.

23. The method of claim 22, wherein an inhalation session corresponds to one selected from a list consisting of:
  i. a sequence of inhalations, the sequence corresponding to a characteristic pattern; and
  ii. a sequence of inhalations, the sequence separated from another session by a pause of more than a threshold duration.

24. A computer program comprising computer executable instructions adapted to cause a computer system to perform the method of claim 22.

* * * * *

UNITED STATES PATENT AND TRADEMARK OFFICE
CERTIFICATE OF CORRECTION

Page 1 of 1

PATENT NO. : 12,302,949 B2
APPLICATION NO. : 17/754940
DATED : May 20, 2025
INVENTOR(S) : Patrick Moloney et al.

It is certified that error appears in the above-identified patent and that said Letters Patent is hereby corrected as shown below:

In the Claims

In Column 18, Claim 4, Line 42, "to the at least a first inhalation" should read as -- to the at least first inhalation --

Signed and Sealed this
Twenty-eighth Day of October, 2025

John A. Squires
*Director of the United States Patent and Trademark Office*